United States Patent [19]
Haaland

[11] Patent Number: 5,863,736
[45] Date of Patent: Jan. 26, 1999

[54] METHOD, APPARATUS AND COMPUTER PROGRAM PRODUCTS FOR DETERMINING QUANTITIES OF NUCLEIC ACID SEQUENCES IN SAMPLES

[75] Inventor: Perry D. Haaland, Chapel Hill, N.C.

[73] Assignee: Becton, Dickinson and Company, Franklin Lakes, N.J.

[21] Appl. No.: 862,905

[22] Filed: May 23, 1997

[51] Int. Cl.$^6$ .............................. C12Q 1/68; C12P 19/34; G06F 17/21
[52] U.S. Cl. .............................. 435/6; 435/91.2; 707/500
[58] Field of Search ........................................ 435/6, 91.2

[56] References Cited

U.S. PATENT DOCUMENTS

| | | |
|---|---|---|
| 5,219,727 | 6/1993 | Wang et al. . |
| 5,270,184 | 12/1993 | Walker et al. .......................... 435/91.2 |
| 5,455,166 | 10/1995 | Walker .................................. 435/91.2 |
| 5,547,861 | 8/1996 | Nadeau et al. .......................... 435/91.2 |
| 5,550,025 | 8/1996 | Walker ........................................ 435/6 |
| 5,593,867 | 1/1997 | Walker et al. .......................... 435/91.2 |
| 5,650,277 | 7/1997 | Novat et al. . |

FOREIGN PATENT DOCUMENTS

| | | | |
|---|---|---|---|
| 0 512 334 A2 | 11/1992 | European Pat. Off. | .......... C12Q 1/68 |
| 0 640 828 A1 | 3/1995 | European Pat. Off. | ........ G01N 21/64 |
| 0 686 699 A2 | 12/1995 | European Pat. Off. | .......... C12Q 1/68 |
| WO95/30139 | 11/1995 | WIPO | ............................ G01N 21/64 |

OTHER PUBLICATIONS

Gibson et al.; "A Method for Real Time Quantitative RT–PCR"; *Genome Research*, 6:995–1001 (1996).

Heid et al.; "Real Time Quantitative PCR"; *Genome Research*, 6:986–994 (1996).

A. Rashtchian; "Amplification of RNA"; *PCR Methods and Applications*, 4:S83–S91 (1994).

Rodriquez et al.; "A Novel Method for the Isolation of Tissue–Specific Genes"; *Nucleic Acids Res.*, 20(13):3528 (1992).

Edmands et al.; "Rapid RT–PCR Amplification from Limited Cell Numbers"; *PCR Methods and Applications*, 3:17–319 (1994).

McCulloch et al.; "An Evaluation of Competitor Type and Size for Use in the Determination of mRNA by Competitive PCR"; *PCR Methods and Applications*, 4:219–226 (1995).

Clementi et al.; "Quantitative PCR and RT–PCR in Virology"; *PCR Methods and Applications*, 2:191–196 (1993).

F. Ferre; "Quantitative or Semi–Quantitative PCR: Reality Versus Myth"; *PCR Methods and Applications*, 2:1–9 (1992).

Tan et al.; "PAF and TNF Increase the Precursor of NF–kappa B p50 mRNA in Mouse Intestine: Quantitative Analysis by Competitive PCR"; *Biochimica et Biophysica Acta*,1215:157–162 (1994).

Kellogg et al.; "Quantitation of HIV–1 Proviral DNA Relative to Cellular DNA by the Polymerase Chain Reaction"; *Analytical Biochemistry*, 189:202–208 (1990).

Holland et al.; "Detection of specific polymerase chain reaction product by utilizing the 5'→3' exonuclease activity of thermus aquaticus DNA polymerase"; *Proc. Natl. Acad. Sci. USA*, 88:7276–7280 (1991).

Walker et al.; "Isothermal in vitro amplification of DNA by a restriction enzyme/DNA polymerase system"; *Proc. Natl. Acad. Sci. USA*, 89:392–296 (1992).

Furtado et al.; "Changes in the Viral mRNA Expression Pattern Correlate with a Rapid Rate of $CD4_+$ T–Cell Number Decline in Human Immunodeficiency Virus Type 1–Infected Individuals"; *J. of Virology*, 69(4):2092–2100 (1995).

Kwoh et al.; "Transcription–based amplification system and detection of amplified human immunodeficiency virus type 1 with a bead–based sandwich hybridization format"; *Proc. Natl. Acad. Sci. USA*, 86:1173–1177 (1989).

Pang et al.; "High levels of unintegrated HIV–1 DNA in brain tissue of AIDS dementia patients"; *Nature*, 343:85–89 (1990).

L. Raeymaekers; "A Commentary on the Practical Applications of Competitive PCR"; *Genome Research*, 6:91–94 (1995).

(List continued on next page.)

Primary Examiner—Eggerton A. Campbell
Attorney, Agent, or Firm—Donna R. Fugit

[57] ABSTRACT

Methods for determining quantities of nucleic acid sequences in samples include the steps of amplifying a plurality of known quantities of a nucleic acid sequence in respective calibration samples and an unknown quantity of a nucleic acid sequence in a test sample, in parallel, during a time interval. These samples may be amplified using an isothermal amplification method such as Strand Displacement Amplification (SDA), or a thermal cycling amplification method such as Polymerase Chain Reaction (PCR), for example. Indicia of the quantities of a nucleic acid sequence being amplified in the calibration and test samples are then measured using conventional techniques, at measurement points in the time interval. Steps are then performed to determine for a first potential cutoff level, a corresponding first set of time points in the time interval at which the indicia of the quantities of a nucleic acid sequence being amplified in each of the calibration samples equal the first cutoff level. This step is then repeated for each of a number of different potential cutoff levels so that respective sets of time points in the time interval can be obtained for each potential cutoff level. According to a preferred aspect of the present invention, a step is then performed to determine, relative to a statistical criterion, which of the sets of points in the time interval better satisfies the statistical criterion against the known quantities of a nucleic acid sequence in the calibration samples. A quantity of a nucleic acid sequence in the test sample is then determined based on the set of points determined to better or best satisfy the statistical criterion. The accuracy of the determination can also be improved using a relatively large number of potential cutoff levels.

45 Claims, 8 Drawing Sheets

OTHER PUBLICATIONS

Piatak, Jr. et al.; "Quantitative Competitive Polymerase Chain Reaction for Accurate Quantitation of HIV DNA and RNA Species"; *Biotechniques*, 14(1):70–80 (1993).

Lizardi et al.; "Exponential Amplification of Recombinant–RNA Hybridization Probes"; *Bio/Technology*, 61197–1202 (1988).

Slamon et al.; "Human Breast Cancer: Correlation of Relapse and Survival with Amplification of the HER–2/neu Oncogene"; *Science*, 235:177–182 (1987).

Sooknanan et al.; "NASBA: A Detection and Amplification System Uniquely Suited for RNA"; *Bio/Technology*, 13:563–564 (1995).

Piatak et al.; "High Levels of HIV–1 ijn Plasma During All Stages of Infection Determined by Competitive PCR"; *Science*, 259:1749–1754 (1993).

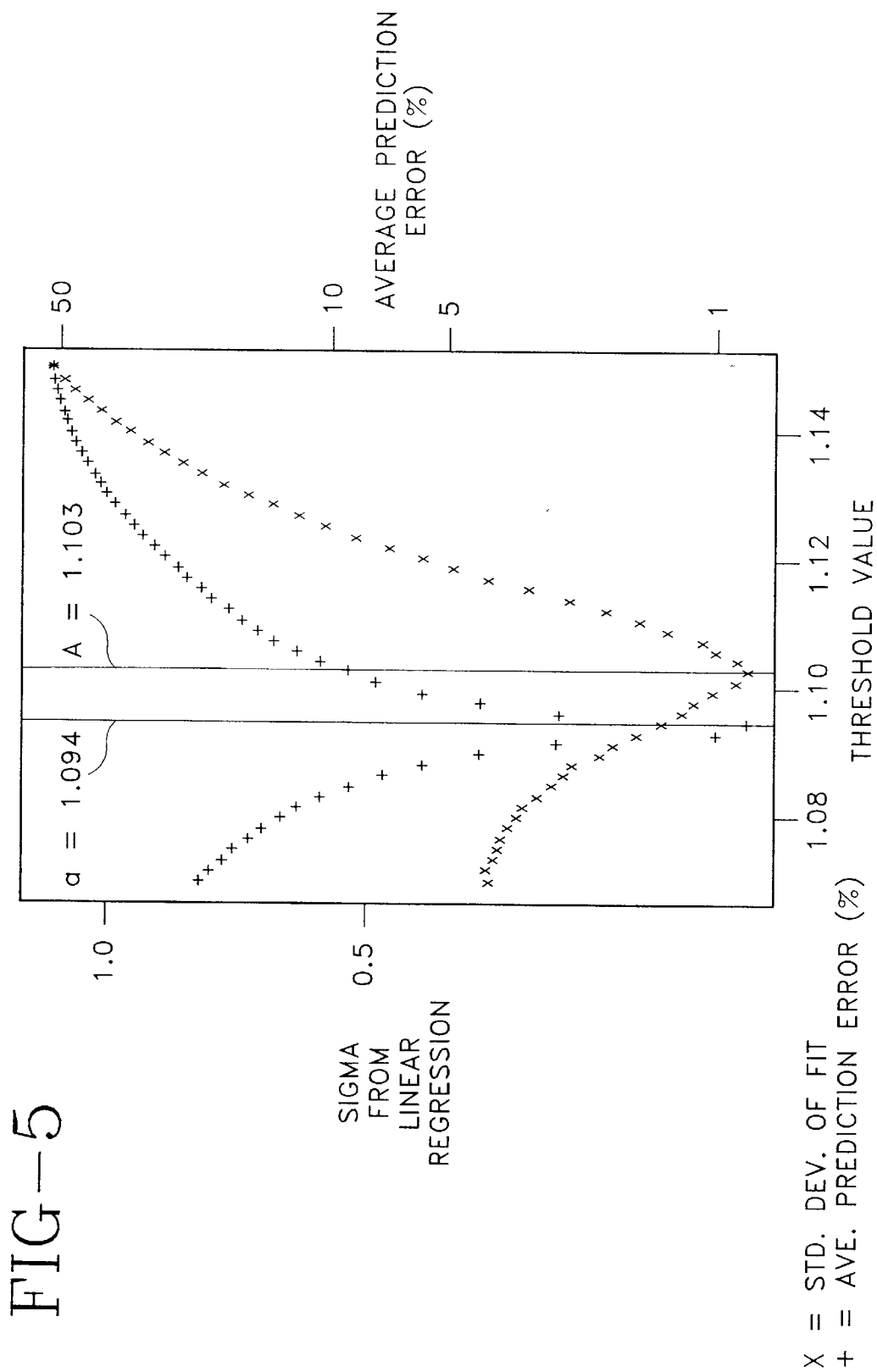

METHOD, APPARATUS AND COMPUTER PROGRAM PRODUCTS FOR DETERMINING QUANTITIES OF NUCLEIC ACID SEQUENCES IN SAMPLES

FIELD OF THE INVENTION

This invention relates to methods, apparatus and computer program products for characterizing nucleic acid sequences, and more particularly to methods, apparatus and computer program products for determining quantities of nucleic acid sequences in samples.

BACKGROUND OF THE INVENTION

Quantitative nucleic sequence analysis plays an increasingly important role in the fields of biological and medical research. For example, quantitative gene analysis has been used to determine the genome quantity of a particular gene, as in the case of the human HER-2 oncogene, which is amplified in approximately 30% of human breast cancers. D. J. Slamon et al., *Science* 235, 177–182 (1987). More recently, gene and genome quantitation have also been used in determining and monitoring the levels of human immunodeficiency virus (HIV) in a patient throughout the different phases of the HIV infection and disease. M. R. Furtado et al., *J. Virol.* 69, 2092–2100 (1995). It has been suggested that higher levels of circulating HIV and failure to effectively control virus replication after infection may be associated with a negative disease prognosis; in other words, there may be an association between virus level (HIV replication) and the pathogenesis of the disease. M. Paitak et al., *Science* 259, 1749–1754 (1993). Accordingly, an accurate determination of HIV nucleic acid levels early in an infection may serve as a useful tool in diagnosing illness, while the ability to correctly monitor the changing levels of viral nucleic acid in one patient throughout the course of an illness may provide clinicians with critical information regarding the effectiveness of treatment and progression of disease. Additionally, the determination of virion-associated HIV RNA levels in plasma represents a marker of viral replication with potential widespread applicability in assessment of the activity of antiretroviral therapy. Id.

Several methods have been described for the quantitative analysis of nucleic acid sequences. The polymerase chain reaction (PCR) and reverse-transcriptase PCR (RT-PCR) have permitted the analysis of small starting quantities of nucleic acid (i.e., as little as one cell equivalent). See, e.g., S. Edmands et al. 1994, *PCR Methods Applic.* 3, 317–19; I. R. Rodriguez et al. 1992, *Nucleic Acids Res.* 20, 3528. Early reports of quantitative PCR report quantitation of the PCR product, but do not measure the initial target sequence quantity. F. Ferre 1992, *PCR Methods Applic.* 2, 1–9. In general, these methods involve measuring PCR product at the end of temperature thermal cycling and relating this level to the starting DNA concentration. Unfortunately, the absolute amount of product generated does not always bear a consistent relationship to the amount of target sequence present at the initiation of the reaction, particularly for clinical specimens. Such an "endpoint" analysis reveals the presence or absence of starting nucleic acid, but generally does not provide an accurate measure of the number of DNA targets. Id. Both the kinetics and efficiency of amplification of a target sequence are dependent on the starting abundance of that sequence, and on the sequence match of the primers and target template, and may also be affected by inhibitors present in the specimen. In PCR analysis of RNA samples, variable efficiencies in both reverse transcription and amplification steps are potential sources of variability. For these reasons, comparison of the amount of specimen-derived PCR product to the amount of product from a separately amplified external control standard does not provide a rigorous basis for quantitation.

One specific approach to nucleic acid amplification is to measure PCR product quantity in the log phase of the reaction prior to the plateau. See, e.g., Kellogg et al. 1990, *Anal. Biochem.* 189, 202–208; S. Pang et al. 1990, *Nature* 343, 85–89. This method requires that each sample has equal input amounts of nucleic acid and that each sample under analysis amplifies with identical efficiency up to quantitative analysis. A gene sequence (contained in all samples at a relatively constant quantity) can be used for sample amplification efficiency normalization. However, using conventional methods of PCR detection and quantitation, it is extremely laborious to assure that all samples are analyzed during the log phase of the reaction, both for the target gene and the normalization gene.

Another method, quantitative competitive PCR (QC-PCR) has been developed and has also been used widely for PCR quantitation. See, e.g., P. D. Siebert and J. W Larrick 1992, *Nature* 359, 557–558; M. J. Piatak et al. 1993, *BioTechniques* 14, 70–81; X. Tan et al. 1994, *Biochim. Biophys. Acta* 1215, 157–162; L. Raeymaekers 1995, *Genome Res.* 5, 91–94. QC-PCR relies on the inclusion of a known amount of an internal control competitor in each reaction mixture. The efficiency of each reaction is normalized to the internal competitor. To obtain relative quantitation, the unknown target PCR product is compared with the known competitor PCR product, usually via gel electrophoresis. The relative amount of target-specific and competitor DNA is measured; this ratio is used to calculate the starting number of target templates. Basically, in this kind of analysis, the larger the ratio of target specific product to competitor specific product, the higher the starting DNA concentration. Success of a QC-PCR assay relies on the development of an internal control that amplifies with the same efficiency as the target molecule. However, the design of the competitor and the validation of amplification efficiencies require much effort. In the QC-PCR method of RNA quantitation, a competitive RNA template matched to the target sequence of interest, but different from it by virtue of an introduced internal deletion, is used in a competitive titration of the reverse transcription and PCR steps, providing stringent internal control. See, e.g., A. Rashtchian 1994, *PCR Methods. Applic.* 4, S83–S91. M. Clementi et al. 1993, *PCR Methods Applic.* 2, 191–196; M. Becker-Andre 1991, *Meth. Molec. Cell. Biol.* 2, 189–201; R. K. McCulloch et al. 1995, *PCR Methods Applic.* 4, 219–226. Increasing amounts of known copy numbers of competitive template are added to replication portions of the test specimen, and quantitation is based on determination of the relative (not absolute) amounts of the differently sized amplified products derived from the wild-type and competitive templates, after electrophoretic separation.

In addition to requiring time-consuming and burdensome downstream processing such as hybridization or gel electrophoresis, these assays are limited in dynamic range (i.e. sensitivity to a range of target nucleic acid concentrations). For example, in competitor assays, the sensitivity to template concentration differences may be compromised when either the target or added competitor DNA is greatly in excess of the other. The dynamic range of the assays that measure the amount of end product can also be limited in that the chosen number of cycles of some reactions may have reached a "plateau" level of product prior to other reactions. See, e.g., L. Raeymaekers, supra. Differences in starting template levels in these reactions may therefore not be well-reflected. Furthermore, small differences in the measured amount of product may result in widely varying estimates of the starting template concentration, leading to inaccuracies due to variable reaction conditions, variations in sampling, or the presence of inhibitors.

In an attempt to reduce the amount of post-amplification analysis required to determine initial nucleic acid quantity, additional methods have been developed to measure nucleic acid amplification in "real time." These methods generally take advantage of fluorescent labels (e.g., fluorescent dyes) that are able to indicate the amount of nucleic acid being amplified, and utilize the relationship between the number of cycles required to achieve a chosen level of fluorescence signal and the concentration of amplifiable targets present at the initiation of the PCR process. For example, European Patent Application No. 94112728 describes a quantitative assay for an amplifiable nucleic acid target sequence which correlates the number of temperature cycles required to reach a certain concentration of target sequence to the amount of target DNA present at the beginning at the PCR process. In this assay system, a set of reaction mixtures are prepared for amplification, with one preparation including an unknown concentration of target sequence and others containing known concentrations (standards) of the sequence. The reaction mixtures also contain a fluorescent dye that fluoresces when bound to double-stranded DNA. The reaction mixtures are thermally cycled in parallel for a number of cycles to achieve a sufficient amplification of the targets. The fluorescence emitted from the reaction mixtures is monitored in real time (i.e. as the amplification reactions occur), and the number of cycles necessary for each reaction mixture to fluoresce to a arbitrary intensity threshold (arbitrary fluorescent value, or AFV) is determined. The number of cycles necessary (CT) for the mixture of unknown nucleic acid to reach the AFV value is then compared to the number of cycles necessary for the known mixtures to reach the AFV value. This method relies on a direct correlation between the number of cycles necessary to achieve a given fluorescence intensity, and the logarithm of concentration of the nucleic acid targets. This relationship is thus used to obtain the initial quantity of target nucleic acid sequence in the mixture of unknown concentration. The method provides for the selection of an arbitrary threshold from which to measure numbers of amplification cycles, in that recorded amplification profiles (amplification curves) are analyzed to find an AFV in which to compare the unknown amplification profiles with the standard amplification profile. However, no particular significance is placed on the initial selection of the AFV or cutoff value, in that an exemplary AFV value is chosen to be in the middle of a range in which all the amplification curves are relatively straight (i.e. in transition from upward exponential amplification to downward curving to an asymptote). Moreover, similar results in nucleic acid quantitation are reported for a fairly broad range of AFV values. One shortcoming of this known method is that below an initial copy number of $10^3$ target sequence molecules, the method is unreliable in accurately determining initial concentration. Another shortcoming of this method is that it assumes that the shape of each amplification curve remains the same, regardless of whether or not it really does. Finally, only a few data points near the arbitrary cutoff value are taken to determine the initial target nucleic acid concentration.

C. A. Heid et al. 1996 (*Genome Research* 6, 986–994) and U. Gibson et al. 1996 (*Genome Research* 6, 995–1001) report methods of real-time quantitative PCR for DNA and RNA quantitation analysis, respectively. Both assays utilize dual-fluorescence reporter systems and are based on the use of the 5'-nuclease assay described by Holland et al. 1991, *Proc. Natl. Acad. Sci. USA* 88, 7276–7280. In these methods, a computer algorithm generates an amplification plot by comparing the amount of reporter dye emission with the number of amplification cycles that have occurred. The algorithm calculates the cycle ($C_T$) at which each PCR amplification reaches an arbitrarily selected (i.e. usually 10 times the standard deviation of the baseline) threshold or cutoff. The relative fluorescent emission threshold is based on the baseline of the reporter dye emission during the first 10–15 amplification cycles. It was demonstrated that the calculated $C_T$ value is proportional to the number of target copies present in the sample. Thus, the $C_T$ value is found to be a quantitative measurement of the copies of the target found in any sample.

As indicated by the foregoing discussion, the prior art teaches that one way to perform quantitative analysis of real-time nucleic acid amplification is to select a number of readings just above and below a chosen cutoff level, fit a linear regression to these points, and solve for the "cycle number" at which the fitted line crosses the cutoff level. The selection of a cutoff level is accordingly somewhat arbitrary, as in selecting a cutoff level about 10 times that of a baseline value, or the maximum value of non-target containing samples, or a certain cutoff level above what has been considered acceptable "noise." One shortcoming of such a cutoff selection criteria is that if the cutoff value corresponds to a time point in the amplification during which the amplification rate is changing (i.e., early in the amplification), a linear fit to the data will be inappropriate.

It has heretofore not been appreciated that small differences in the selection of cutoff levels used in quantitation algorithms may have a substantial effect on the ultimate quality (i.e., accuracy) of quantitation. There remains a need to provide an objective and automatic method of selecting preferred cutoff values that will allow users of amplification methods to determine the initial concentrations of target nucleic acids more accurately and reliably than present methods. There also remains a need to provide for methods of determining dynamic cutoff levels that can be easily varied from one experiment or determination to another.

SUMMARY OF THE INVENTION

It is therefore an object of the present invention to provide improved methods, apparatus and computer program products for determining quantities of nucleic acid sequences in test samples.

It is also an object of the present invention to provide methods, apparatus and computer program products for more accurately measuring quantities of nucleic acid sequences in test samples, using a plurality of calibration and control samples containing respective known quantities of the nucleic acid sequence therein.

These and other objects, features and advantages are provided, according to the present invention, by methods, apparatus and computer program products for determining quantities of nucleic acid sequences being amplified, using a preferred cutoff level which is determined by a statistical criterion. In particular, according to one embodiment of the present invention, a plurality of known quantities of a nucleic acid sequence in respective calibration samples (i.e., standards) and an unknown quantity of the nucleic acid sequence in a test sample are amplified in parallel during a time interval. These samples may be amplified using an isothermal amplification reaction method such as Strand Displacement Amplification (SDA) or a thermal cycling reaction method such as the Polymerase Chain Reaction (PCR), for example. Indicia of the quantities of the nucleic acid sequence being amplified in the calibration and test samples are then measured using conventional techniques, at measurement points in the time interval. The indicia of the quantities of the nucleic acid sequence being amplified may take the form of fluorescence signals (e.g., fluorescence intensities or detectable fluorescent energy transfer) if the samples contain fluorescent indicators therein (e.g., fluorescent dyes, labels, intercalators, etc). Other indicia that are suitable for real-time measurement (e.g., radioactive signals) may also be used.

A step is then performed to determine for a first potential cutoff level, a corresponding first set of time points in the time interval at which the measured indicia of the quantities of the nucleic acid sequence being amplified in each of the calibration samples equal the first cutoff level. This step is then repeated for each of a number of different potential cutoff levels so that respective sets of time points in the time interval can be obtained for each potential cutoff level. According to a preferred aspect of the present invention, a step is then performed to determine, relative to a statistical criterion, which of the sets of points in the time interval better satisfies the statistical criterion against the known quantities of the nucleic acid sequence in the calibration samples. A quantity of the nucleic acid sequence in the test sample is then determined based on the set of points determined to better or best satisfy the statistical criterion.

For example, the step to determine which of the sets of points better satisfies the statistical criterion may comprise the step of determining which of the sets of points in the time interval provides a better linear fit against logarithms of the known starting quantities of the nucleic acid sequence in the calibration samples. Preferably, this step comprises the steps of fitting regression lines to respective "graphs" of each of the sets of time points in the time interval versus logarithms of the known starting quantities of the nucleic acid sequence in the calibration samples. Standard deviations of the fits between each of the sets of time points and respective regression lines are then determined. The set of time points preferably corresponding to the lowest standard deviation of fit is then used to select the preferred cutoff level from the potential cutoff levels and then determine the starting quantity of the nucleic acid in the test sample based on the preferred cutoff level. This advantageous result is preferably achieved by determining a time at which the measured indicia of the quantities of the nucleic acid sequence in the test sample equals the preferred cutoff level and then fitting that time to the "preferred" regression line corresponding to the preferred set of time points. The logarithm of the starting concentration of the nucleic acid sequence in the test sample can then be determined from the preferred regression line.

According to another preferred aspect of the present invention, a curve fitting operation is performed to more accurately estimate the preferred indicia cutoff level (e.g., preferred fluorescence signal cutoff level). In particular, respective "data" curves are preferably fit to "graphs" of discrete points of the measured fluorescence signals of individual calibration and test samples versus points in the time interval at which the corresponding fluorescence signals were measured. Here, a non-parametric curve smoothing operation may be performed after the discrete points have been normalized to a common baseline. As determined by the inventors herein, it is possible to even further improve the accuracy of the preferred indicia cutoff level by determining lower confidence limit curves for each of the "smoothed" data curves. The lower confidence limit curves may also be smoothed using a non-parametric smoothing operation. Each of the above-described sets of time points in the time interval can then be determined by determining intersections between each of the smoothed lower confidence limit curves and the respective potential cutoff levels.

As described above, a set of time points corresponding to a lowest standard deviation of fit can be used to accurately determine a preferred cutoff level and then determine the starting quantity of the nucleic acid in the test sample based on the preferred cutoff level. However, according to another aspect of the present invention, control samples containing known starting quantities of the nucleic acid sequence can also be used to facilitate determination of a preferred cutoff level. In particular, after respective regression lines have been fit for each set of time points in the time interval corresponding to the calibration samples, an average prediction error (APE) can be determined between each regression line and those of a respective set of time points corresponding to the control samples. The potential cutoff level corresponding to the regression line having the lowest average prediction error associated therewith can then be used to determine the starting concentration of the nucleic acid sequence in the test sample.

Another preferred embodiment of the present invention includes an apparatus for determining a quantity of a nucleic acid sequence in a test sample. This preferred apparatus comprises means, such as a fluorescence measurement tool, for measuring indicia of the quantities of a nucleic acid sequence being amplified in at least one test sample, containing an unknown starting quantity of the nucleic acid sequence therein, and also being amplified in a plurality of calibration samples, containing respective known starting quantities of the nucleic acid sequence therein, at respective measurement points in the time interval. A computer program product is also provided for controlling operation of the measuring means and performing numerical operations relating to the above-described steps.

In particular, the preferred computer program product comprises a computer readable storage medium having computer-readable program code means embodied in the medium. The preferred computer-readable program code means comprises computer-readable program code means for determining, for a first potential indicia cutoff level, first points in the time interval at which the indicia of the quantities of the nucleic acid sequence being amplified in the calibration samples equal the first cutoff level. Program code means is also preferably provided for determining, for a second potential indicia cutoff level, second points in the time interval at which the indicia of the quantities of the nucleic acid sequence being amplified in the calibration samples equal the second cutoff level. In addition, the program code means determines, relative to a statistical criterion, such as the lowest standard deviation of fit to a regression line or the lowest average prediction error relative to a regression line, which of the first or second plurality of points in the time interval better satisfies the statistical criterion against the known quantities of the nucleic acid sequence in the calibration samples. The starting quantity of the nucleic acid sequence in the test sample is then determined, based on those of the first or second points determined to better satisfy the statistical criterion. Preferred program code means is also provided for performing more detailed ones of the above-described steps as numerical operations. The present invention therefore provides a tool which can more accurately determine the quantities of nucleic acid sequences in test samples, by more accurately determining the cutoff levels at which measurements of indicia of the quantities of the nucleic acid sequences in calibration samples are evaluated.

BRIEF DESCRIPTION OF THE DRAWINGS

FIG. 5 is a graphical illustration comparing preferred fluorescence cutoff levels determined using different statistical criterion.

DESCRIPTION OF PREFERRED EMBODIMENTS

Figure 1:
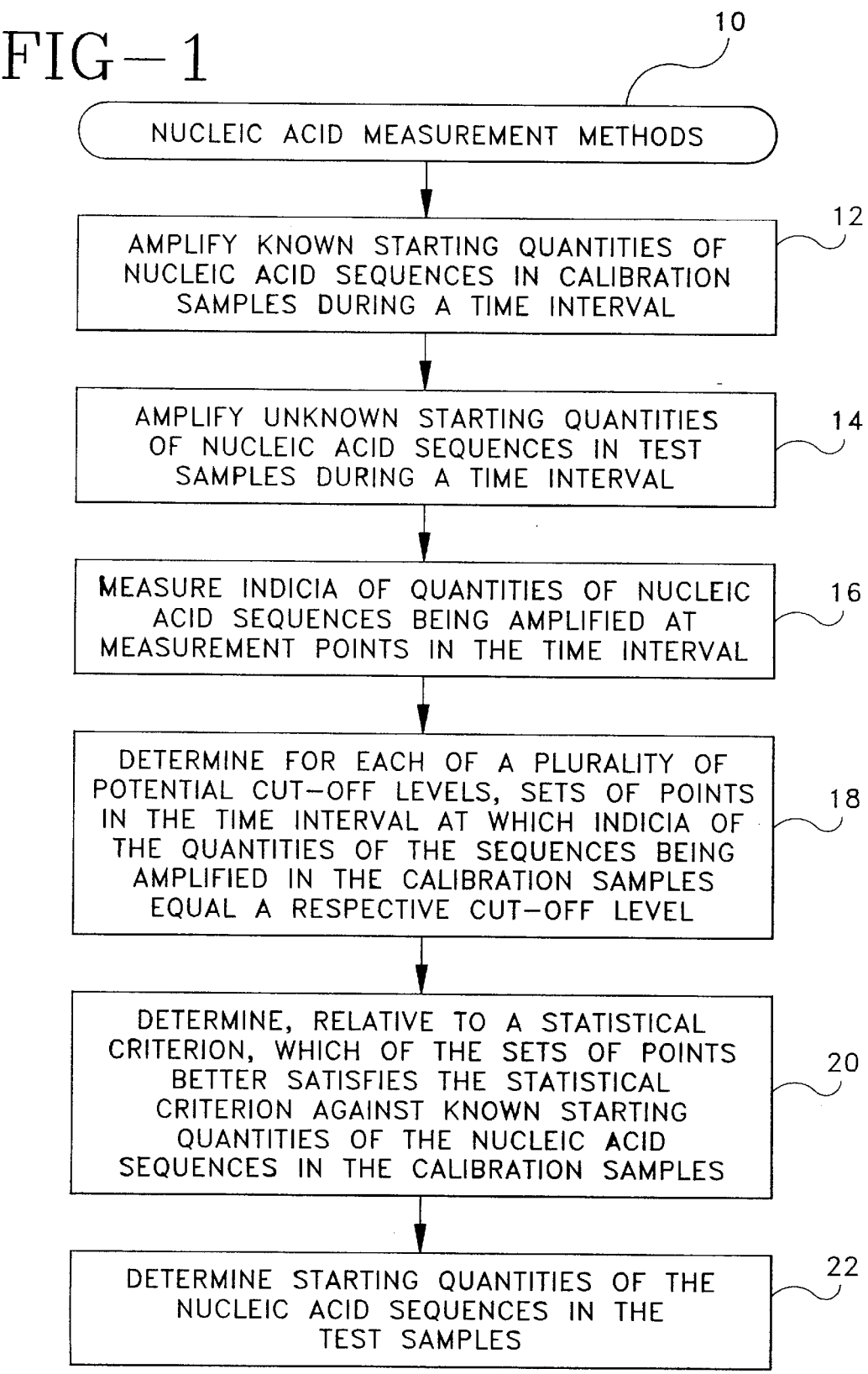
FIG. 1 is a flow chart illustrating steps performed by methods of determining quantities of nucleic acid sequences in samples, according to the present invention.

The present invention will now be described more fully hereinafter with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Referring to FIGS. 1–5, preferred methods 10 of determining quantities of nucleic acid sequences in samples will now be more fully described. These methods include the steps 12, 14 of amplifying a plurality of known starting quantities of a nucleic acid sequence (e.g., RNA, DNA) in respective calibration samples (i.e., standards) and also amplifying an unknown starting quantity of the nucleic acid sequence in at least one test sample during respective time intervals. Preferably, the nucleic acid sequences in the calibration and test samples are the same, however, the samples may possibly contain different nucleic acid sequences or different quantities of different nucleic acid sequences may be amplified in parallel in one composite sample. These amplification steps may be performed using conventional techniques and may be performed separately for each sample during respective nonoverlapping time intervals. These separate time intervals may then be normalized to a common starting time and time interval for purposes of analysis. More preferably, however, the steps 12, 14 of amplifying each of the nucleic acid sequences in the calibration and test samples are performed in parallel on separate samples, during a single time interval.

As will be understood by those skilled in the art, the samples may be amplified according to any known nucleic acid amplification method, including both thermal cycling amplification methods and isothermal amplification methods. The present invention is advantageous in enhancing quantitation of nucleic acids amplified by either thermal cycling methods or isothermal methods, although the present invention may provide particular advantages to isothermal amplification methods. Suitable thermal cycling methods useful in the practice of the present invention include, but are not limited to, the Polymerase Chain Reaction (PCR; U.S Pat. Nos. 4,683,202, 4,683,195 and 4,965,188); Reverse Transcriptase PCR (RT-PCR); DNA Ligase Chain Reaction (LCR; International Patent Application No. WO 89/09835); and transcription-based amplification (D. Y. Kwoh et al. 1989, *Proc. Natl. Acad. Sci. USA* 86, 1173–1177). Suitable isothermal amplification methods useful in the practice of the present invention include, but are not limited to, Strand Displacement Amplification (SDA; Walker et al. 1992, *Proc. Nati. Acad. Sci. USA* 89, 392–396); Q-β replicase (Lizardi et al. 1988, *Bio/Technology* 6, 1197–1202); Nucleic Acid-Based Sequence Amplification (NASBA; R. Sooknanan and L. Malek 1995, *Bio/Technology* 13, 563–65); and Self-Sustained Sequence Replication (3SR; Guatelli et al. 1990, *Proc. Nati. Acad. Sci. USA* 87, 1874–1878). Exemplary SDA methods are described in U.S. Pat. Nos. 5,445,166 to Walker and 5,270,184 to Walker et al., the disclosures of which are incorporated herein by reference.

Indicia of the quantities of the nucleic acid sequence being amplified in the calibration and test samples are then measured at respective measurement points in the time interval, step 16, using a measurement tool such as the Model 7700 Sequence Detector, manufactured and distributed by Applied Biosystems, a division of Perkin Elmer, Foster City, Calif., or the Fluoroskan II, manufactured by LabSystems, Inc., Rochester, N.Y. The indicia of the quantities of the nucleic acid sequence being amplified in the calibration and test samples may take the form of fluorescence signals (e.g., fluorescence intensities or fluorescent energy transfer) if the samples contain fluorescence indicators (e.g., fluorescent labels) therein. Accordingly, the measurement tool may contain one or more photodetectors for measuring the fluorescence signals from the samples undergoing parallel amplification. The measurement tool may also contain a computer-controlled stepper motor so that each calibration and test sample can be arranged as an array of samples and automatically and repeatedly positioned opposite a photodetector during the step of measuring fluorescence intensity. A preferred measurement tool is more fully described hereinbelow with reference to FIG. 6.

As provided above, the indicia of target nucleic acid concentration may take the form of fluorescent signals, although those skilled in the art will appreciate that other indicia of nucleic acid concentration are known and may be used in the practice of the present invention. To illustrate, indicia of nucleic acid concentration may be provided by labels that produce signals detectable by fluorescence, radioactivity, colorimetry, X-ray diffraction or absorption, magnetism, or enzymatic activity. Suitable labels include, for example, fluorophores, chromophores, radioactive isotopes (e.g., $^{32}P$ or $^{125}I$), electron-dense reagents, enzymes, and ligands having specific binding partners (e.g., biotinavidin). Labeling of nucleic acids may be achieved by a number of means, including by chemical modification of a nucleic acid primer or probe. Suitable fluorescent labels may include non-covalently binding labels (e.g., intercalating dyes) such as ethidium bromide, propidium bromide, chromomycin, acridine orange, and the like. However, in the practice of the present invention the use of covalently-binding fluorescent agents is preferred. Such covalently-binding fluorescent labels include fluorescein and derivatives thereof such as FAM, HEX, TET and JOE (all of which can be obtained from the Applied Biosystems Division of Perkin Elmer, Foster City, Calif.); rhodamine and derivatives such as Texas Red (Molecular Probes, Eugene, Oreg.); ROX and TAMRA (Applied Biosystems, Foster City, Calif.); Lucifer Yellow; coumarin derivatives and the like. Another preferred indicia of nucleic acid concentration is fluorescence energy-transfer (FET), in which a fluorescent reporter (or "donor") label and a quencher (or "acceptor") label are used in tandem to produce a detectable signal that is proportional to the amount of amplified nucleic acid product (e.g., in the form of double-stranded nucleic acid) present in the reaction mixture. Yet another detection method useful in the practice of the present invention is fluorescence polarization (FP) detection of nucleic acid amplification, described in U.S. Pat. No. 5,593,867 to Walker et al., and incorporated herein in its entirety.

After measuring indicia of quantities of nucleic acid sequences at step 16, a step 18 is then performed to determine for a first potential cutoff level (e.g., a first normalized fluorescence level), a corresponding first set of time points in the time interval at which the indicia (e.g., fluorescence signal) of the quantities of the nucleic acid sequence being amplified in each of the calibration and test samples equal the first cutoff level. This step is then repeated for each of a plurality of different potential cutoff levels so that respective sets of time points in the time interval can be obtained for each potential cutoff level. As described more fully hereinbelow, the "indicia" (e.g., fluorescence signals) may be unfiltered indicia (i.e., raw data) or the indicia may be filtered, for example, by generating a lower confidence limit curve from the unfiltered indicia.

According to a preferred aspect of the present invention, a step 20 is then performed to determine, relative to a statistical criterion, which of the sets of points in the time interval better satisfies the statistical criterion against the known quantities of the nucleic acid sequence in the calibration samples. A quantity of the nucleic acid sequence in the test sample is then determined based on the set of points determined to better or best satisfy the statistical criterion. For example, as explained more fully hereinbelow with reference to FIGS. 2–5, the step of determining which of the sets of time points better satisfies the statistical criterion may comprise the step of determining which of the sets of time points in the time interval provides a better linear fit against logarithms of the known starting quantities of the nucleic acid sequence in the calibration samples. Preferably, this step comprises the steps of fitting regression lines to respective "graphs" of each of the sets of time points in the time interval versus logarithms of the known starting quantities of the nucleic acid sequence in the calibration samples. Standard deviations of the fits between each of the sets of time points and respective regression lines are then determined. The set of time points preferably corresponding to the lowest standard deviation of fit is then used to select the preferred cutoff level and then determine the starting quantity of the nucleic acid sequence in the test sample based on the preferred cutoff level.

Determination of the set of points which better satisfies the statistical criterion is preferably achieved by determining a time at which the filtered (or unfiltered) fluorescence signal of the test sample equals the preferred cutoff level and then fitting that time to the "preferred" regression line corresponding to the preferred set of time points. A step 22 is then performed to determine the starting concentration of the nucleic acid sequence in the test samples from the preferred regression line. According to another aspect of the present invention, control samples containing known starting quantities of the nucleic acid sequence can also be used to facilitate determination of a preferred cutoff level. In particular, after respective regression lines have been fit for each set of time points in the time interval corresponding to the calibration samples, an average prediction error (APE) can be determined between each regression line and those of a respective set of time points corresponding to the control samples. The potential cutoff level corresponding to the regression line having the lowest average prediction error associated therewith can then be used to determine the starting concentration of the nucleic acid sequence in the test sample. Other statistical criterion may also be used. For example, a cross-validation prediction error may be minimized to enable determination of a starting concentration. Alternatively, if multiple different criterion are used, as "average" of the preferred cutoff levels achieved by each different criterion may be used.

As described more fully hereinbelow, the step 18 of determining sets of points in the time interval for each of the potential cutoff levels may include the initial steps of fitting curves to respective graphs of the measured indicia of the quantities of the nucleic acid sequence being amplified in respective calibration or test samples versus respective measurement time points, using a non-parametric smoothing operation. Here, the amplification of each sample can be represented by a set of discrete data points containing a set of x-values consisting of measurement time points and a corresponding set of y-values consisting of measured fluorescence signals. These x- and y-values for each sample are normalized to a common baseline using conventional techniques and then a non-parametric smoothing operation is performed on each of the sets of x- and y-values.

In particular, for each set of x- and y-values which correspond to a respective calibration or test sample and make up a respective amplification curve, a wavelet fit is obtained and a smooth amplification curve is obtained via a waveshrink operation which is commercially available in the S+WAVELETS™ module of the S-PLUS™ software package. This software package is commercially available from MathSoft, Inc., Seattle, Wash. As will be understood by those skilled in the art, an estimate of the noise in the sets of x- and y-values and/or a standard deviation ($\sigma$) about the smoothed curve is typically generated by the preferred smoothing operation.

Next, according to another preferred aspect of the present invention, a respective lower confidence limit curve (LCL) is determined for each amplification curve so that an estimate of the amplification time needed to reach a potential cutoff level can be determined with reduced susceptibility to noise in the measured indicia (y-values) or local irregularities in the amplification rates. Each lower confidence limit curve may be determined, for example, by subtracting $2\sigma$ (or other preferred value) in fluorescence signal from the y-values for each smoothed amplification curve. Each lower confidence limit curve is also preferably "smoothed" using a non-parametric smoothing operation such as a thin-plate splines operation which can be obtained from the FUNFITS module in the STATLIB programming archive. This archive is available on the world wide web at http://lib.stat.cmu.edu. These lower confidence limit curves represent a relationship between measured indicia, as filtered, and time.

For purposes of illustration, an application of the above-described operations will now be described. In particular, referring to FIG. 2, x-y graphs of unfiltered normalized indicia of the quantities of a nucleic acid sequence (i.e., fluorescence signal) being amplified in a plurality of calibration and test samples versus time (i.e., amplification curves), are illustrated. Wavelet smoothing operations were also performed, as described above, to generate a smooth curve for each of the amplification curves. These smooth curves are illustrated by the solid lines. In this application, calibration samples (i.e., standards) were prepared for amplification by spiking 0, 0, 40, 400, 4000, 15,000 and 40,000 target copies of a nucleic acid sequence into reaction buffers using techniques known to those skilled in the art. These calibration samples are illustrated by the legend in FIG. 2 as CS1=0, CS2=0, CS3=40, CS4=400, CS5=4,000, CS6=15,000 and CS7=40,000. To verify the accuracy of the present invention, six "unknown" test samples were also prepared. Three of the test samples were spiked with 1,144 target copies of the nucleic acid sequence and the three other test samples were spiked with 10,560 target copies. These test samples are illustrated by the legend as T1=1,144, T2=1,144, T3=1,144, T4=10,560, T5=10,560 and T6=10, 560. These six test samples were also treated as control samples to illustrate a statistical criterion based on average prediction error (APE), as explained more fully hereinbelow.

Figure 2:
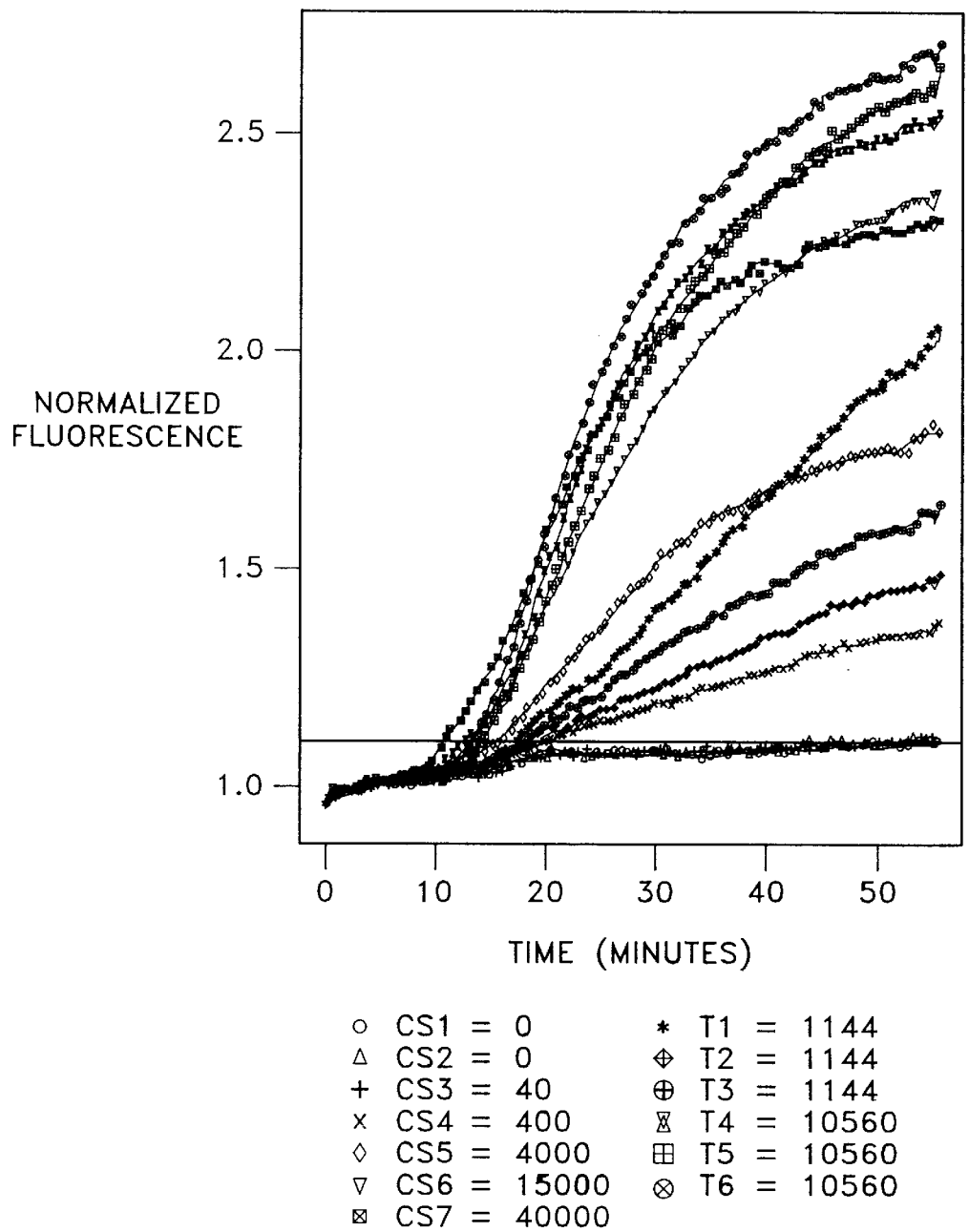
FIG. 2 is a graphical illustration of amplification data for calibration and test samples containing quantities of a nucleic acid sequence therein.

Numerical operations are then performed on the amplification curves (CS1–7 and T1–6) of FIG. 2 to generate respective lower confidence limit curves which illustrate relationships between "filtered" fluorescence signals and amplification time. In particular, waveshrink operations can be performed to generate smoothed amplification curves and determine a respective standard deviation about each curve. Lower confidence limit curves can then be determined by "filtering" the amplification curves by subtracting "$2\sigma$" from the fluorescence signal at each measurement time point. This operation is preferably performed so that subsequently determined estimates of the amplification times needed to reach a potential fluorescence cutoff level can be determined with reduced susceptibility to noise or local irregularities. The "smoothed" lower confidence limit curves (SLCL) can then be determined by performing a thin plate spline fit to each of the lower confidence limit curves, using the aforementioned software package. Other smoothing techniques can also be used. Such techniques may include kernal smoothers, cubic splines, b-splines and locally weighted regression, for example. An adequately expansive range of potential fluorescence cutoff levels ($FCL_L$-$FCL_H$) can then be selected. As determined by the inventor herein, accurate selection of a preferred cutoff level is critical to the accurate determination of the starting quantity of a nucleic acid sequence in a test sample.

Figure 3:
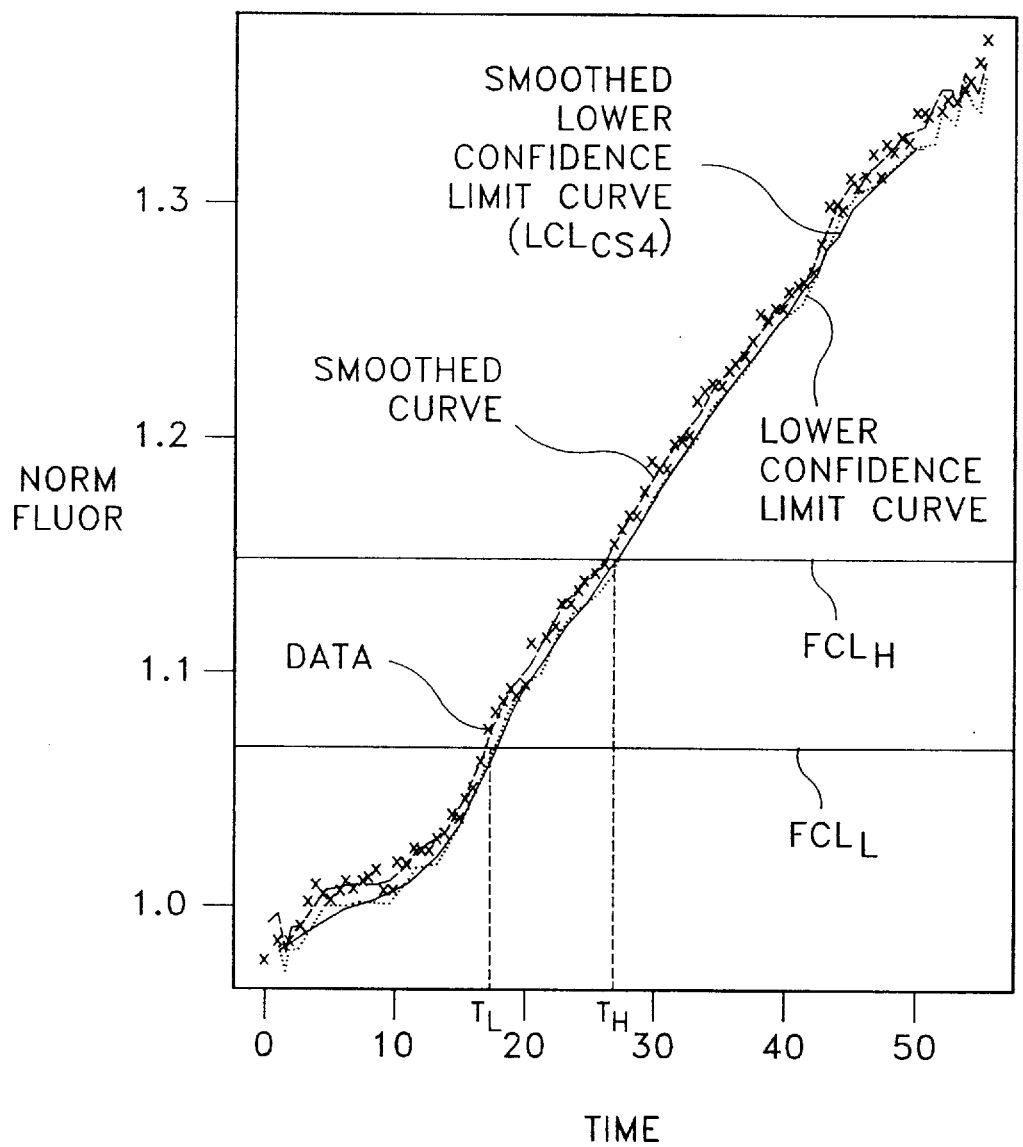
FIG. 3 is a graphical illustration of amplification data and smooth curves determined therefrom using a non-parametric smoothing operation, according to the present invention.

To illustrate, the above described operations can be performed to determine a smoothed lower confidence limit curve ($SLCL_{CS4}$) from the amplification data corresponding to the fourth calibration sample CS4. This lower confidence limit curve is best illustrated by FIG. 3. The same operations are then performed to generate smoothed lower confidence limit curves from each of the other amplification curves corresponding to the other samples. Intersections between each of the smoothed lower confidence limit curves and each of a plurality of spaced potential fluorescence cutoff levels in the range ($FCL_L$-$FCL_H$) are then numerically determined, using techniques known to those skilled in the art. Sets of time points along the x-axis in the range $T_L$-$T_H$ are then determined from the intersections between a respective fluorescence cutoff level and each of the smoothed lower confidence limit curves which intersect the respective cutoff level.

Figure 4A:
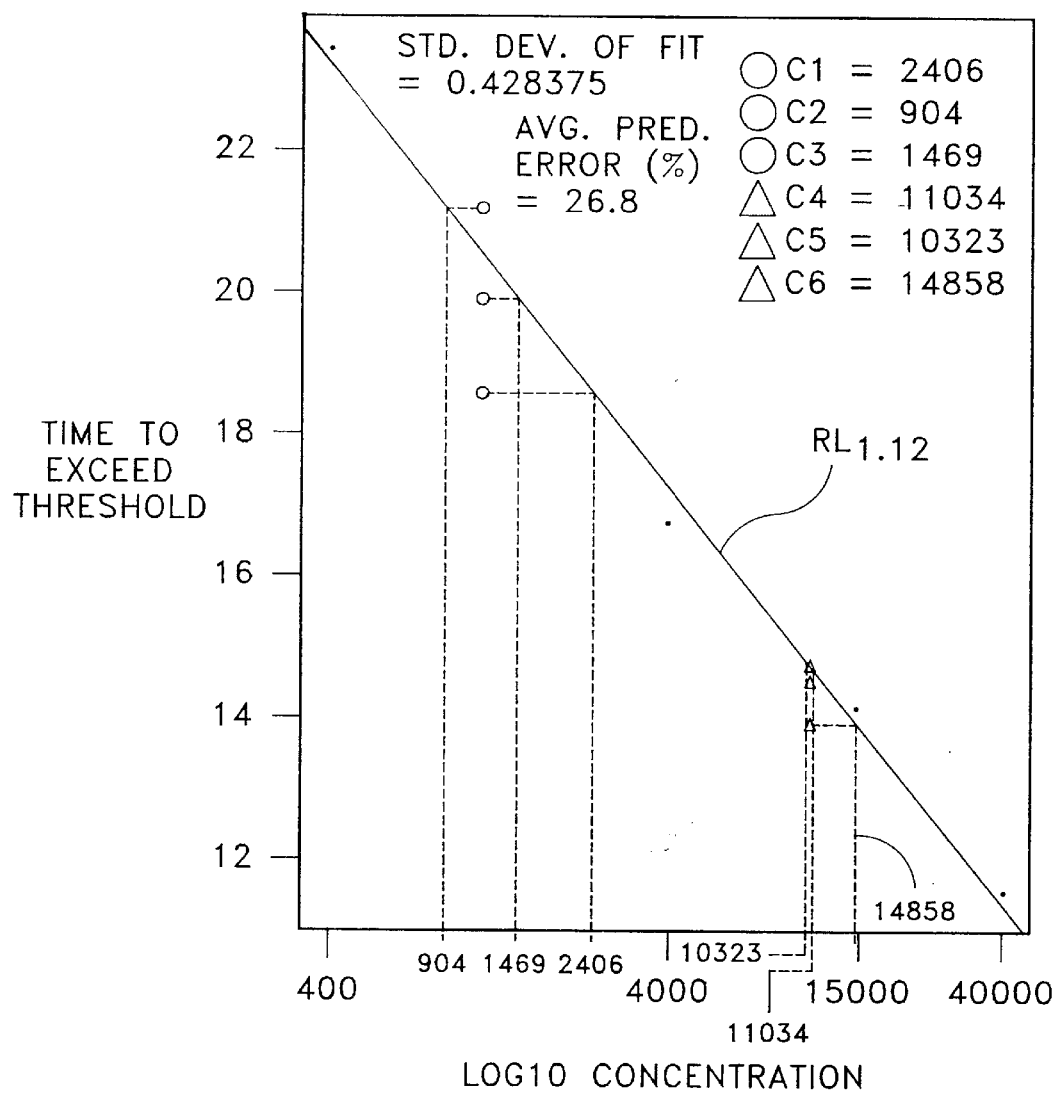
FIG. 4A is a graphical illustration of time to exceed a potential cutoff level versus nucleic acid starting concentration, for a potential fluorescence cutoff level of 1.12.

Referring now to FIG. 4A and using a potential fluorescence cutoff level of 1.12 as an example, a graph of the time points (determined from the intersections between each of the SLCL curves and a horizontal line at y=1.12) versus logarithms of the known starting concentrations of the calibration samples (x-axis) can be determined. A regression line ($RL_{1.12}$) can then be fit to the graph of the time points versus the logarithms of the known starting concentrations, as illustrated. Using conventional techniques well known to those skilled in the art, a standard deviation of the fit between the regression line and points in the graph is also determined to be 0.428. The, using a potential fluorescence cutoff level of 1.103, a graph of the time points (determined from the intersections between each of the SLCL curves and a horizontal line at y=1.103) versus logarithms of the known starting concentrations of the calibration samples (x-axis) is determined, as illustrated best by FIG. 4B. A regression line ($RL_{1.103}$) is then fit to the graph of the time points versus the logarithms of the known starting concentrations. A standard deviation of the fit between the regression line and the points in the graph is then determined to be 0.180. Finally, using a potential fluorescence cutoff level of 1.094, a graph of the time points (determined from the intersections between each of the SLCL curves and a horizontal line at y=1.094) versus logarithms of the known starting concentrations of the calibration samples (x-axis) can be determined, as illustrated best by FIG. 4C. A regression line ($RL_{1.094}$) is then fit to the graph of the time points versus the logarithms of the known starting concentrations, as illustrated. A standard deviation of the fit between the regression line and the points in the graph is then determined to be 0.226.

As described above, the cutoff level yielding the lowest standard deviation of fit is then used to map the intersections, between the selected cutoff level and the smoothed lower confidence limit curves corresponding to the test samples, to the logarithms of the starting concentrations of the test samples. For example, based on an analysis of just three potential fluorescence cutoff levels in the range $FCL_L$-$FCL_H$, the regression line $RL_{1.103}$ corresponding to a normalized fluorescence cutoff level of 1.103 should be used to determine the starting concentration of the test samples T1–T6.

According to another embodiment of the present invention, a plurality of "control" samples having known concentrations of the nucleic acid sequence therein can be amplified in parallel with the calibration and test samples. The times corresponding to the intersections (i.e., intersection times) between a potential fluorescence cutoff level (e.g., 1.12, 1.103 and 1.094) and the smoothed lower confidence limit curves corresponding to the control samples, can then be compared to respective regression lines. An average prediction error can then be determined as the arithmetic average of each of the errors in time between a respective intersection time and the corresponding "intersection time" predicted by the regression line at the known starting concentration of the control sample.

Figure 4B:
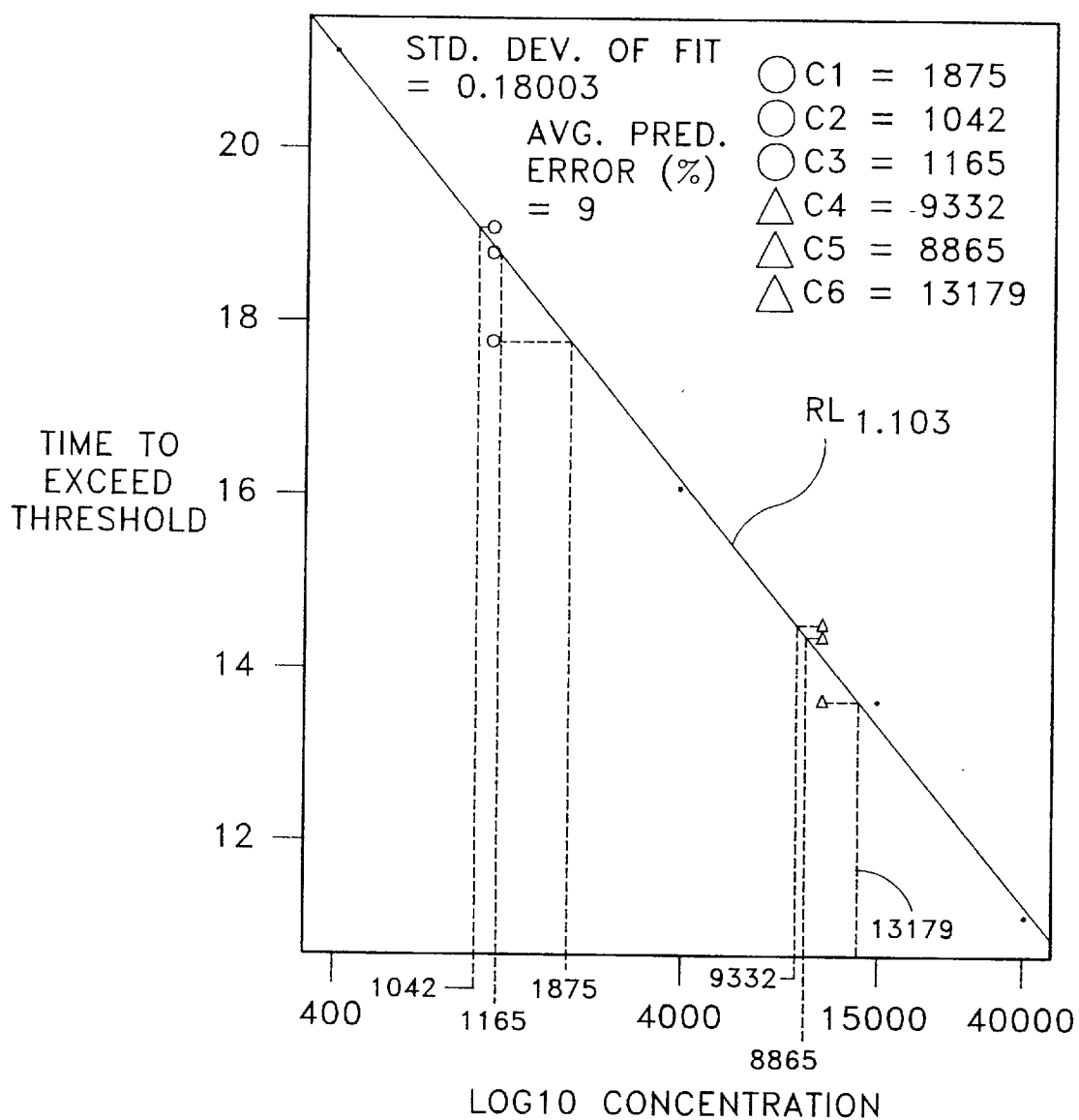
FIG. 4B is a graphical illustration of time to exceed a potential cutoff level versus nucleic acid starting concentration, for a potential fluorescence cutoff level of 1.103.
Figure 4C:
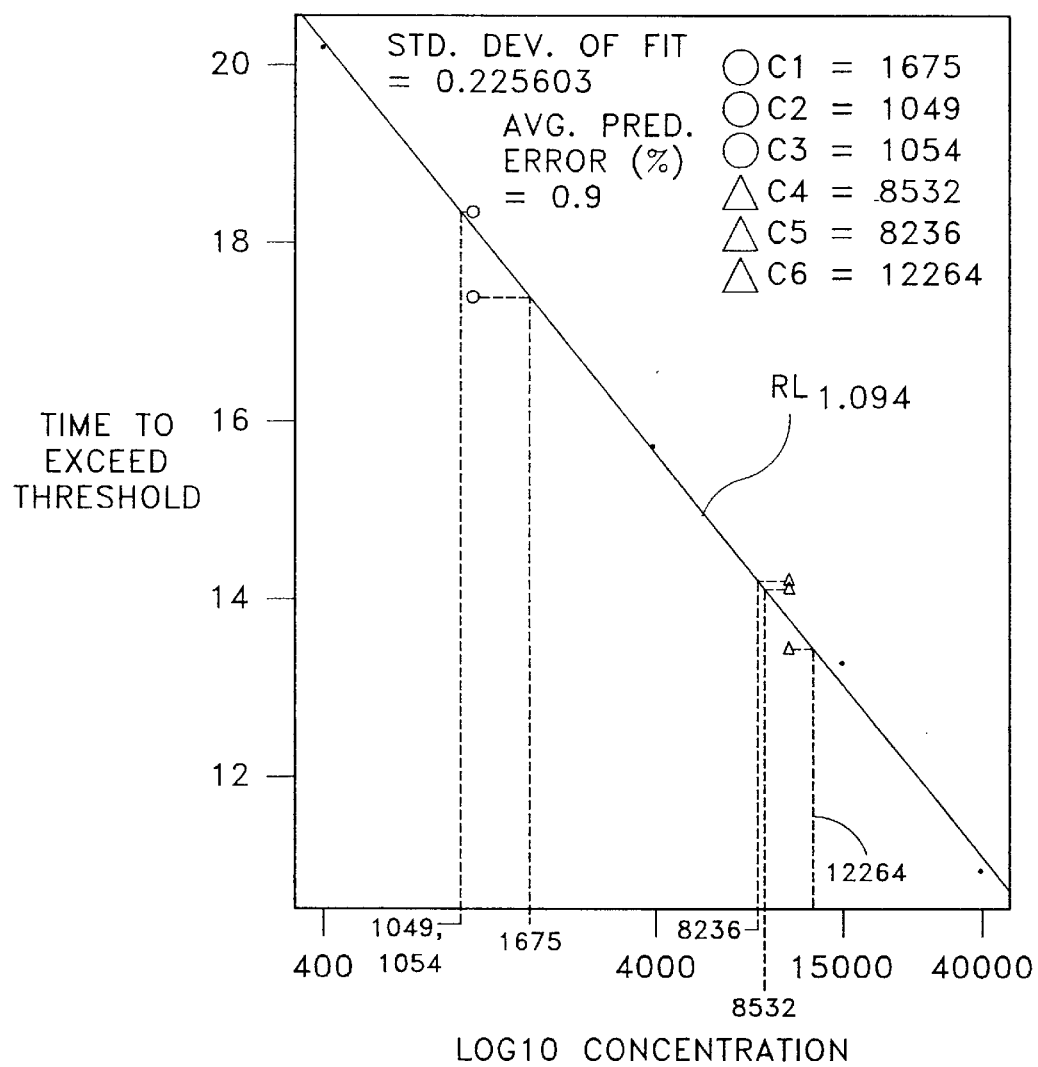
FIG. 4C is a graphical illustration of time to exceed a potential cutoff level versus nucleic acid starting concentration, for a potential fluorescence cutoff level of 1.094.

Based on the regression line of FIG. 4A, an average prediction error (APE) of 26.8% is determined if the "test" samples T1–T6 (having known starting concentrations therein) are treated as control samples C1–C6 for purposes of illustration only. As shown by the legend of FIG. 4A, the known starting concentrations of the test samples (i.e., 1,144 and 10,560 target copies) are predicted as between 904–2,406 target copies for "control" samples C1–C3 and as between 10,323–14,858 target copies for control samples C4–C6. Based on the regression line of FIG. 4B, an average prediction error (APE) of 9% is found for the "control" samples C1–C6. Finally, as shown by the legend of FIG. 4B, the known starting concentrations of the test samples are predicted as between 1,042–1,875 target copies for control samples C1–C3 and as between 8,865–13,179 target copies for control samples C4–C6. Based on the regression line of FIG. 4C, an average prediction error (APE) of 0.9% is found for the "control" samples C1–C6. As shown by the legend of FIG. 4C, the known starting concentrations of the test samples are predicted as between 1,049–1,675 target copies for control samples C1–C3 and as between 8,236–12,264 target copies for control samples C4–C6. According to this embodiment, the cutoff level yielding the lowest average prediction error is then preferably used to map the intersections between the selected cutoff level and the smoothed lower confidence limit curves corresponding to the test samples, to the logarithms of the starting concentrations of the test samples. For example, based on the APE analysis for just three potential fluorescence cutoff levels in the range $FCL_L$-$FCL_H$, the regression line $RL_{1.094}$ corresponding to a normalized fluorescence cutoff level of 1.094 should be used to determine the starting concentration of the test samples T1–T6.

Referring now to FIG. 5, a comparison between the two above-described statistical criterion is illustrated. In particular, a plot of the standard deviation of fit to a regression line versus potential cutoff level yields a preferred cutoff level of 1.103. A plot of the average prediction error (APE) versus potential cutoff level yields a preferred cutoff level of 1.094 which is relatively close to 1.103. As will be understood by those skilled in the art, FIG. 5 illustrates the dependence of two measures of "goodness" in the calibration, namely, precision (standard deviation about the regression line) and average bias (average prediction error), on the choice of the cutoff levels. Thus, reasonable choices in statistical criterion can yield cutoff levels that are approximately equal. Furthermore, as illustrated by the large number of x-y data points in FIG. 5, more accurate estimates of the starting quantities of the nucleic acid sequence in the test samples may be determined by using a greater number of closely spaced potential cutoff levels.

Figure 6:
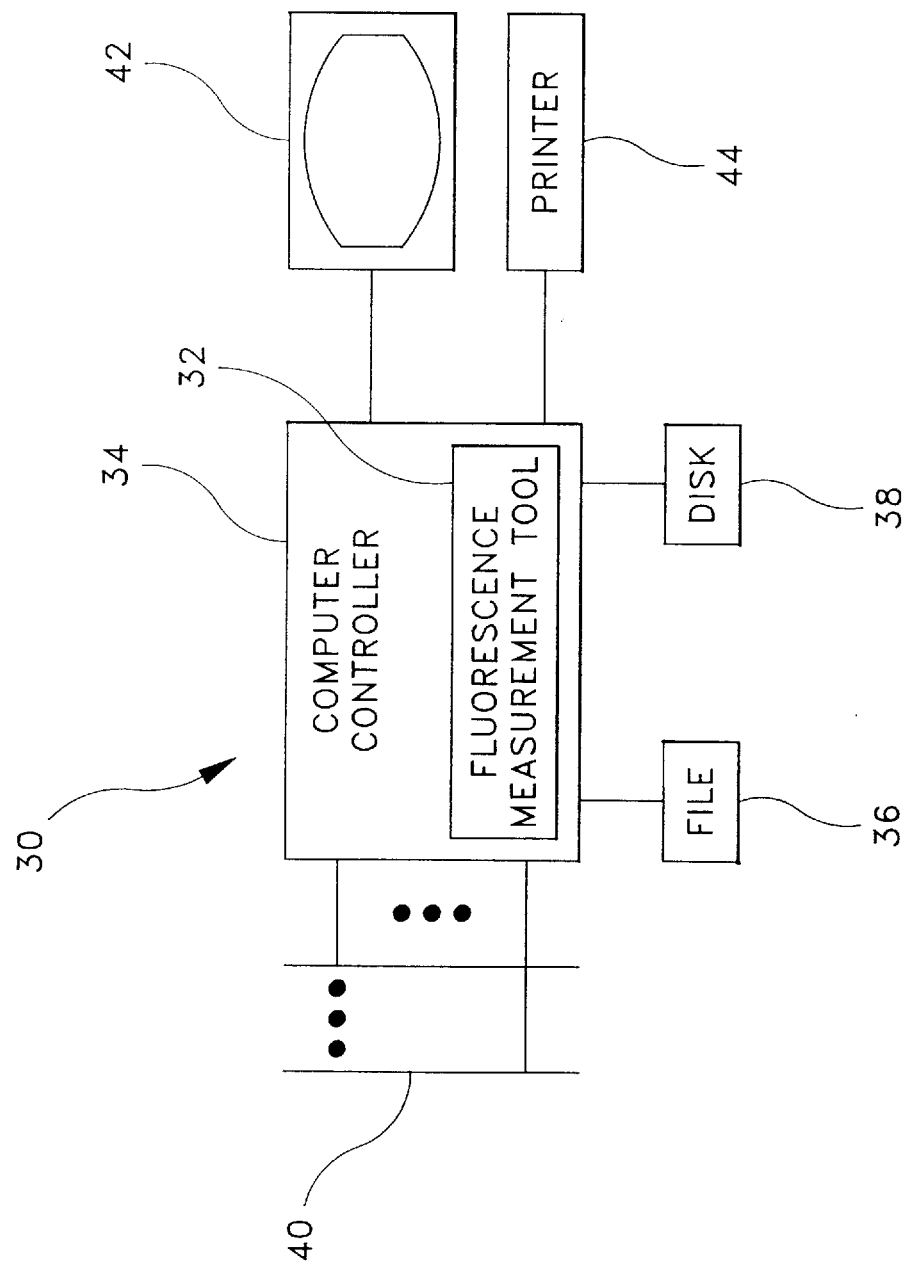
FIG. 6 illustrates a general hardware description of apparatus for determining quantities of nucleic acid sequences in test samples, according to the present invention.

Another preferred embodiment of the present invention includes an apparatus 30 for determining quantities of nucleic acid sequences in test samples as illustrated by FIG. 6. This preferred apparatus comprises means 32, such as the aforementioned fluorescence measurement tool, for measuring indicia of the quantities of a nucleic acid sequence being amplified in at least one test sample (containing an unknown starting quantity of the nucleic acid sequence therein) and in a plurality of calibration samples (containing respective known starting quantities of the nucleic acid sequence therein), at respective measurement points in the time interval. The apparatus 30 also operates under computer control. In particular, the measurement tool 32 is preferably operatively coupled to a general purpose or application specific computer controller 34. The controller 34 preferably comprises a computer program product for controlling operation of the measurement tool 32 and performing numerical operations relating to the above-described steps. The controller 34 may accept set-up and other related data via a file 36, disk input 38 or data bus 40. A display 42 and printer 44 are also preferably provided to visually display the operations performed by the controller 34. It will be understood by those having skill in the art that the functions performed by the controller 34 may be realized in whole or in part as software modules running on a general purpose computer system. Alternatively, a dedicated stand-alone system with application specific integrated circuits for performing the above described functions and operations may be provided.

In particular, a preferred computer program product comprises a computer readable storage medium having computer-readable program code means embodied in the medium. The preferred computer-readable program code means comprises computer-readable program code means for determining, for a first potential fluorescence cutoff level, first points in the time interval at which the indicia of the quantities of the nucleic acid sequence being amplified in the calibration samples equal the first cutoff level. Program code means is also preferably provided for determining, for a second potential fluorescence cutoff level, second points in the time interval at which the indicia of the quantities of the nucleic acid sequence being amplified in the calibration samples equal the second cutoff level. In addition, the program code means determines, relative to a statistical criterion, such as the lowest standard deviation of fit to a regression line or the lowest average prediction error relative to a regression line, which of the first or second plurality of points in the time interval better satisfies the statistical criterion against the known quantities of the nucleic acid sequence in the calibration samples. The starting quantity of the nucleic acid sequence in the test sample is then determined, based on those of the first or second points determined to better satisfy the statistical criterion. Preferred program code means is also provided for performing more detailed ones of the above-described steps as numerical operations. The present invention therefore provides a tool which can more accurately determine the quantities of nucleic acid sequences in test samples, by more accurately determining the cutoff levels at which measurements of indicia of the quantities of the nucleic acid sequences in calibration samples are evaluated.

In the drawings and specification, there have been disclosed typical preferred embodiments of the invention and, although specific terms are employed, they are used in a generic and descriptive sense only and not for purposes of limitation, the scope of the invention being set forth in the following claims. Moreover, the terminology in the claims relating to graphs, fitting lines and curves to graphs and determining curves, is intended to include the processing of data (e.g., x-y data) and variables internal to a processing unit (e.g., computer) containing memory and as will be understood by those skilled in the art is not limited to the physical acts of printing or plotting lines, curves, and graphs.

That which is claimed is:

1. A method of determining a quantity of a nucleic acid sequence in a sample, comprising the steps of:
   amplifying a plurality of known quantities of a nucleic acid sequence in respective calibration samples and an unknown quantity of a nucleic acid sequence in a test sample, during a time interval;
   measuring indicia of the quantities of a nucleic acid sequence being amplified in the calibration and test samples, at measurement points in the time interval;
   determining for a first cutoff level, first points in the time interval at which the indicia of the quantities of a nucleic acid sequence being amplified in the calibration samples equal the first cutoff level, based on the measured indicia of the quantities of a nucleic acid sequence being amplified in the calibration samples;

determining for a second cutoff level, second points in the time interval at which the indicia of the quantities of a nucleic acid sequence being amplified in the calibration samples equal the second cutoff level, based on the measured indicia of the quantities of a nucleic acid sequence being amplified in the calibration samples;

determining, relative to a statistical criterion, which of the first or second points in the time interval better satisfies the statistical criterion against the known quantities of a nucleic acid sequence in the calibration samples; and determining a quantity of a nucleic acid sequence in the test sample, based on those of the first or second points determined to better satisfy the statistical criterion.

2. The method of claim 1, wherein the calibration and test samples contain a fluorescent indicator therein; and wherein said step of measuring indicia of the quantities of a nucleic acid sequence being amplified comprises measuring fluorescence signals from the calibration and test samples at the measurement points in the time interval.

3. The method of claim 2, wherein said amplifying step comprises amplifying a plurality of known quantities of a nucleic acid sequence in respective calibration samples and an unknown quantity of a nucleic acid sequence in a test sample, in parallel.

4. The method of claim 1, wherein said step of determining which of the first or second points in the time interval better satisfies the statistical criterion comprises the step of determining which of the first or second points in the time interval provides a better linear fit against logarithms of the known quantities of a nucleic acid sequence in the calibration samples.

5. The method of claim 4, wherein said step of determining which of the first or second points in the time interval provides a better linear fit comprises the steps of:

fitting a first regression line to a graph of the first points versus logarithms of the known quantities of a nucleic acid sequence in the calibration samples;

fitting a second regression line to a graph of the second points versus logarithms of the known quantities of a nucleic acid sequence in the calibration samples;

determining a standard deviation of the fit between the first points and the first regression line; and determining a standard deviation of the fit between the second points and the second regression line.

6. The method of claim 5, wherein said step of determining first points in the time interval comprises the steps of:

fitting a first curve to a graph of the measured indicia of the quantity of a nucleic acid sequence being amplified in a first of the calibration samples versus first ones of the measurement points in the time interval, using a non-parametric smoothing operation;

determining a first lower confidence limit curve from the first curve;

fitting a second curve to a graph of the measured indicia of the quantity of a nucleic acid sequence being amplified in a second of the calibration samples versus second ones of the measurement points in the time interval, using a non-parametric smoothing operation;

determining a second lower confidence limit curve from the second curve;

determining first intersections between the first cutoff level and the first and second lower confidence limit curves; and determining the first points in the time interval from the first intersections.

7. The method of claim 1, wherein said step of determining first points in the time interval comprises the steps of:

fitting a first curve to a graph of the measured indicia of the quantity of a nucleic acid sequence being amplified in a first of the calibration samples versus first ones of the measurement points in the time interval, using a non-parametric smoothing operation;

determining a first lower confidence limit curve from the first curve;

fitting a second curve to a graph of the measured indicia of the quantity of a nucleic acid sequence being amplified in a second of the calibration samples versus second ones of the measurement points in the time interval, using a non-parametric smoothing operation;

determining a second lower confidence limit curve from the second curve;

determining first intersections between the first cutoff level and the first and second lower confidence limit curves; and determining the first points in the time interval from the first intersections.

8. The method of claim 7, wherein the calibration and test samples contain a fluorescent indicator therein; and wherein said step of measuring indicia of the quantities of a nucleic acid sequence being amplified comprises measuring fluorescence signals from the calibration and test samples at the measurement points in the time interval.

9. The method of claim 8, wherein said amplifying step comprises amplifying a plurality of known quantities of a nucleic acid sequence in respective calibration samples and an unknown quantity of a nucleic acid sequence in a test sample, in parallel.

10. The method of claim 9, wherein said step of determining which of the first or second points in the time interval better satisfies the statistical criterion comprises the step of determining which of the first or second points in the time interval provides a better linear fit against logarithms of the known quantities of a nucleic acid sequence in the calibration samples.

11. The method of claim 10, wherein said step of determining which of the first or second points in the time interval provides a better linear fit comprises the steps of:

fitting a first regression line to a graph of the first points versus the logarithms of the known quantities of a nucleic acid sequence in the calibration samples;

fitting a second regression line to a graph of the second points versus the logarithms of the known quantities of a nucleic acid sequence in the calibration samples;

determining a standard deviation of the fit between the first points and the first regression line; and determining a standard deviation of the fit between the second points and the second regression line.

12. The method of claim 1, wherein said step of determining first points in the time interval comprises the steps of:

fitting a first curve to a graph of the measured indicia of the quantity of a nucleic acid sequence being amplified in a first of the calibration samples versus first ones of the measurement points in the time interval, using a non-parametric smoothing operation;

fitting a second curve to a graph of the measured indicia of the quantity of a nucleic acid sequence being amplified in a second of the calibration samples versus second ones of the measurement points in the time interval, using a non-parametric smoothing operation;

determining first intersections between the first cutoff level and the first and second curves; and determining the first points in the time interval from the first intersections.

13. The method of claim 1, wherein said step of determining first points in the time interval comprises the steps of:

fitting a first curve to a graph of the measured indicia of the quantity of a nucleic acid sequence being amplified in a first of the calibration samples versus first ones of the measurement points in the time interval, using a non-parametric smoothing operation;

determining a first lower confidence limit curve from the first curve, using a non-parametric smoothing operation;

fitting a second curve to a graph of the measured indicia of the quantity of a nucleic acid sequence being amplified in a second of the calibration samples versus second ones of the measurement points in the time interval, using a non-parametric smoothing operation;

determining a second lower confidence limit curve from the second curve using a non-parametric smoothing operation;

determining first intersections between the first cutoff level and the first and second lower confidence limit curves; and determining the first points in the time interval from the first intersections.

14. The method of claim 13, wherein said step of determining second points in the time interval comprises the steps of:

determining second intersections between the second cutoff level and the smoothed first and second lower confidence limit curves; and determining the second points in the time interval from the second intersections.

15. The method of claim 1, wherein said amplifying step comprises amplifying a plurality of known quantities of a nucleic acid sequence in respective calibration and respective control samples and an unknown quantity of a nucleic acid sequence in a test sample, during the time interval;

wherein said step of determining first points in the time interval comprises determining, for a first cutoff level, first points in the time interval at which the indicia of the quantities of a nucleic acid sequence being amplified in the calibration and control samples equal the first cutoff level, based on the measured indicia of the quantities of a nucleic acid sequence being amplified in the calibration samples; and wherein said step of determining which of the first or second points in the time interval better satisfies the statistical criterion comprises the steps of fitting a first line to a graph of the first points versus logarithms of the known quantities of a nucleic acid sequence in the calibration samples and then determining an average prediction error between those of the first points corresponding to the control samples and the first line.

16. The method of claim 6, wherein said amplifying step comprises amplifying a plurality of known quantities of a nucleic acid sequence in respective calibration and respective control samples and an unknown quantity of a nucleic acid sequence in a test sample, during the time interval;

wherein said step of determining first points in the time interval comprises determining, for a first cutoff level, first points in the time interval at which the indicia of the quantities of a nucleic acid sequence being amplified in the calibration and control samples equal the first cutoff level, based on the measured indicia of the quantities of a nucleic acid sequence being amplified in the calibration samples; and wherein said step of determining which of the first or second points in the time interval better satisfies the statistical criterion comprises the steps of fitting a first line to a graph of the first points versus logarithms of the known quantities of a nucleic acid sequence in the calibration samples and then determining an average prediction error between those of the first points corresponding to the control samples and the first line.

17. The method of claim 7, wherein said amplifying step comprises amplifying a plurality of known quantities of a nucleic acid sequence in respective calibration and respective control samples and an unknown quantity of a nucleic acid sequence in a test sample, during the time interval;

wherein said step of determining first points in the time interval comprises determining, for a first cutoff level, first points in the time interval at which the indicia of the quantities of a nucleic acid sequence being amplified in the calibration and control samples equal the first cutoff level, based on the measured indicia of the quantities of a nucleic acid sequence being amplified in the calibration samples; and wherein said step of determining which of the first or second points in the time interval better satisfies the statistical criterion comprises the steps of fitting a first line to a graph of the first points versus logarithms of the known quantities of a nucleic acid sequence in the calibration samples and then determining an average prediction error between those of the first points corresponding to the control samples and the first line.

18. The method of claim 1, wherein said step of determining first points in the time interval comprises the steps of:

determining a first lower confidence limit curve from a graph of the measured indicia of the quantity of a nucleic acid sequence being amplified in a first of the calibration samples versus first ones of the measurement points in the time interval;

determining a second lower confidence limit curve from a graph of the measured indicia of the quantity of a nucleic acid sequence being amplified in a second of the calibration samples versus second ones of the measurement points in the time interval;

determining first intersections between the first cutoff level and the first and second lower confidence limit curves; and determining the first points in the time interval from the first intersections.

19. The method of claim 5, wherein said step of determining first points in the time interval comprises the steps of:

determining a first lower confidence limit curve from a graph of the measured indicia of the quantity of a nucleic acid sequence being amplified in a first of the calibration samples versus first ones of the measurement points in the time interval;

determining a second lower confidence limit curve from a graph of the measured indicia of the quantity of a nucleic acid sequence being amplified in a second of the calibration samples versus second ones of the measurement points in the time interval;

determining first intersections between the first cutoff level and the first and second lower confidence limit curves; and determining the first points in the time interval from the first intersections.

20. An apparatus for determining a quantity of a nucleic acid sequence in a test sample, comprising:

means for measuring indicia of the quantities of a nucleic acid sequence being amplified in a test sample, containing an unknown starting quantity of a nucleic acid sequence therein, and in a plurality of calibration samples, containing respective known quantities of a nucleic acid sequence therein, at measurement points in a time interval; and a computer program product comprising a computer readable storage medium having computer-readable program code means embodied in said medium, said computer-readable program code means comprising:

computer-readable program code means for determining for a first cutoff level, first points in the time interval at which the indicia of the quantities of a nucleic acid sequence being amplified in the calibration samples equal the first cutoff level, based on the measured indicia of the quantities of a nucleic acid sequence being amplified in the calibration samples;

computer-readable program code means for determining for a second cutoff level, second points in the time interval at which the indicia of the quantities of a nucleic acid sequence being amplified in the calibration samples equal the second cutoff level, based on the measured indicia of the quantities of a nucleic acid sequence being amplified in the calibration samples;

computer-readable program code means for determining, relative to a statistical criterion, which of the first or second points in the time interval better satisfies the statistical criterion against the known quantities of a nucleic acid sequence in the calibration samples; and computer-readable program code means for determining a quantity of a nucleic acid sequence in the test sample, based on those of the first or second points determined to better satisfy the statistical criterion.

21. The apparatus of claim 20, wherein said measuring means comprises means for measuring fluorescent intensity of the calibration and test samples at the measurement points in the time interval.

22. The apparatus of claim 21, wherein said computer-readable program code means for determining which of the first or second points in the time interval better satisfies the statistical criterion comprises means for determining which of the first or second points in the time interval provides a better linear fit against logarithms of the known quantities of a nucleic acid sequence in the calibration samples.

23. The apparatus of claim 20, wherein said computer-readable program code means for determining first points in the time interval comprises:

computer-readable program code means for fitting a first curve to a graph of the measured indicia of the quantity of a nucleic acid sequence being amplified in a first of the calibration samples versus first ones of the measurement points in the time interval;

computer-readable program code means for determining a first lower confidence limit curve from the first curve;

computer-readable program code means for fitting a second curve to a graph of the measured indicia of the quantity of a nucleic acid sequence being amplified in a second of the calibration samples versus second ones of the measurement points in the time interval;

computer-readable program code means for determining a second lower confidence limit curve from the second curve;

computer-readable program code means for determining first intersections between the first cutoff level and the first and second lower confidence limit curves; and computer-readable program code means for determining the first points in the time interval from the first intersections.

24. The apparatus of claim 20, wherein said computer-readable program code means for determining first points in the time interval comprises:

computer-readable program code means for fitting a first curve to a graph of the measured indicia of the quantity of a nucleic acid sequence being amplified in a first of the calibration samples versus first ones of the measurement points in the time interval, using a non-parametric smoothing operation;

computer-readable program code means for determining a first lower confidence limit curve from the first curve;

computer-readable program code means for fitting a second curve to a graph of the measured indicia of the quantity of a nucleic acid sequence being amplified in a second of the calibration samples versus second ones of the measurement points in the time interval, using a non-parametric smoothing operation;

computer-readable program code means for determining a second lower confidence limit curve from the second curve;

computer-readable program code means for determining first intersections between the first cutoff level and the first and second lower confidence limit curves; and computer-readable program code means for determining the first points in the time interval from the first intersections.

25. The apparatus of claim 20, wherein said computer-readable program code means for determining first points in the time interval comprises:

computer-readable program code means for fitting a first curve to a graph of the measured indicia of the quantity of a nucleic acid sequence being amplified in a first of the calibration samples versus first ones of the measurement points in the time interval, using a non-parametric smoothing operation;

computer-readable program code means for determining a first lower confidence limit curve from the first curve, using a non-parametric smoothing operation;

computer-readable program code means for fitting a second curve to a graph of the measured indicia of the quantity of a nucleic acid sequence being amplified in a second of the calibration samples versus second ones of the measurement points in the time interval, using a non-parametric smoothing operation;

computer-readable program code means for determining a second lower confidence limit curve from the second curve, using a non-parametric smoothing operation;

computer-readable program code means for determining first intersections between the first cutoff level and the first and second smoothed lower confidence limit curves; and computer-readable program code means for determining the first points in the time interval from the first intersections.

26. An apparatus for determining a quantity of a nucleic acid sequence in a test sample, comprising:
   means for measuring indicia of the quantities of a nucleic acid sequence being amplified in a test sample, containing an unknown starting quantity of a nucleic acid sequence therein, and in a plurality of calibration samples, containing respective known quantities of a nucleic acid sequence therein, at measurement points in a time interval; and
   a computer program product readable by the apparatus and tangibly embodying a program of instructions executable by the apparatus to perform the method steps of:
   determining for a first cutoff level, first points in the time interval at which the indicia of the quantities of a nucleic acid sequence being amplified in the calibration samples equal the first cutoff level, based on the measured indicia of the quantities of a nucleic acid sequence being amplified in the calibration samples;
   determining for a second cutoff level, second points in the time interval at which the indicia of the quantities of a nucleic acid sequence being amplified in the calibration samples equal the second cutoff level, based on the measured indicia of the quantities of a nucleic acid sequence being amplified in the calibration samples;
   determining, relative to a statistical criterion, which of the first or second points in the time interval better satisfies the statistical criterion against the known quantities of a nucleic acid sequence in the calibration samples; and
   determining a quantity of a nucleic acid sequence in the test sample, based on those of the first or second points determined to better satisfy the statistical criterion.

27. The apparatus of claim 26, wherein said step of determining which of the first or second points in the time interval better satisfies the statistical criterion comprises the step of determining which of the first or second points in the time interval provides a better linear fit against logarithms of the known quantities of a nucleic acid sequence in the calibration samples.

28. The apparatus of claim 27, wherein said step of determining which of the first or second points in the time interval provides a better linear fit comprises the steps of:
   fitting a first regression line to a graph of the first points versus logarithms of the known quantities of a nucleic acid sequence in the calibration samples;
   fitting a second regression line to a graph of the second points versus logarithms of the known quantities of a nucleic acid sequence in the calibration samples;
   determining a standard deviation of the fit between the first points and the first regression line; and
   determining a standard deviation of the fit between the second points and the second regression line.

29. The apparatus of claim 28, wherein said step of determining first points in the time interval comprises the steps of:
   fitting a first curve to a graph of the measured indicia of the quantity of a nucleic acid sequence being amplified in a first of the calibration samples versus first ones of the measurement points in the time interval;
   determining a first lower confidence limit curve from the first curve;
   fitting a second curve to a graph of the measured indicia of the quantity of a nucleic acid sequence being amplified in a second of the calibration samples versus second ones of the measurement points in the time interval;
   determining a second lower confidence limit curve from the second curve;
   determining first intersections between the first cutoff level and the first and second lower confidence limit curves; and
   determining the first points in the time interval from the first intersections.

30. The apparatus of claim 26, wherein said step of determining first points in the time interval comprises the steps of:
   fitting a first curve to a graph of the measured indicia of the quantity of a nucleic acid sequence being amplified in a first of the calibration samples versus first ones of the measurement points in the time interval;
   determining a first lower confidence limit curve from the first curve;
   fitting a second curve to a graph of the measured indicia of the quantity of a nucleic acid sequence being amplified in a second of the calibration samples versus second ones of the measurement points in the time interval;
   determining a second lower confidence limit curve from the second curve;
   determining first intersections between the first cutoff level and the first and second lower confidence limit curves; and
   determining the first points in the time interval from the first intersections.

31. The apparatus of claim 30, wherein the calibration and test samples contain a fluorescent indicator therein; and wherein said step of measuring indicia of the quantities of a nucleic acid sequence being amplified comprises measuring fluorescence signals from the calibration and test samples at the measurement points in the time interval.

32. The apparatus of claim 31, wherein said amplifying step comprises amplifying a plurality of known quantities of a nucleic acid sequence in respective calibration samples and an unknown quantity of a nucleic acid sequence in a test sample, in parallel.

33. The apparatus of claim 32, wherein said step of determining which of the first or second points in the time interval better satisfies the statistical criterion comprises the step of determining which of the first or second points in the time interval provides a better linear fit against logarithms of the known quantities of a nucleic acid sequence in the calibration samples.

34. The apparatus of claim 33, wherein said step of determining which of the first or second points in the time interval provides a better linear fit comprises the steps of:
   fitting a first regression line to a graph of the first points versus the logarithms of the known quantities of a nucleic acid sequence in the calibration samples;
   fitting a second regression line to a graph of the second points versus the logarithms of the known quantities of a nucleic acid sequence in the calibration samples;
   determining a standard deviation of the fit between the first points and the first regression line; and
   determining a standard deviation of the fit between the second points and the second regression line.

35. The apparatus of claim 34, wherein said step of determining first points in the time interval comprises the steps of:

fitting a first curve to a graph of the measured indicia of the quantity of a nucleic acid sequence being amplified in a first of the calibration samples versus first ones of the measurement points in the time interval;

fitting a second curve to a graph of the measured indicia of the quantity of a nucleic acid sequence being amplified in a second of the calibration samples versus second ones of the measurement points in the time interval;

determining first intersections between the first cutoff level and the first and second curves; and determining the first points in the time interval from the first intersections.

36. A computer program product readable by a machine having means operatively coupled thereto for measuring indicia of quantities of a nucleic acid sequence being amplified in a test sample, containing an unknown starting quantity of a nucleic acid sequence therein, and in a plurality of calibration samples, containing respective known quantities of a nucleic acid sequence therein, at measurement points in a time interval, and tangibly embodying a program of instructions executable by the machine to perform the method steps of:

determining for a first cutoff level, first points in the time interval at which the indicia of the quantities of a nucleic acid sequence being amplified in the calibration samples equal the first cutoff level, based on the measured indicia of the quantities of a nucleic acid sequence being amplified in the calibration samples;

determining for a second cutoff level, second points in the time interval at which the indicia of the quantities of a nucleic acid sequence being amplified in the calibration samples equal the second cutoff level, based on the measured indicia of the quantities of a nucleic acid sequence being amplified in the calibration samples;

determining, relative to a statistical criterion, which of the first or second points in the time interval better satisfies the statistical criterion against the known quantities of a nucleic acid sequence in the calibration samples; and determining a quantity of a nucleic acid sequence in the test sample, based on those of the first or second points determined to better satisfy the statistical criterion.

37. The computer program product of claim 36, wherein said step of determining which of the first or second points in the time interval better satisfies the statistical criterion comprises the step of determining which of the first or second points in the time interval provides a better linear fit against logarithms of the known quantities of a nucleic acid sequence in the calibration samples.

38. The computer program product of claim 37, wherein said step of determining which of the first or second points in the time interval provides a better linear fit comprises the steps of:

fitting a first regression line to a graph of the first points versus logarithms of the known quantities of a nucleic acid sequence in the calibration samples;

fitting a second regression line to a graph of the second points versus logarithms of the known quantities of a nucleic acid sequence in the calibration samples;

determining a standard deviation of the fit between the first points and the first regression line; and determining a standard deviation of the fit between the second points and the second regression line.

39. The computer program product of claim 38, wherein said step of determining first points in the time interval comprises the steps of:

fitting a first curve to a graph of the measured indicia of the quantity of a nucleic acid sequence being amplified in a first of the calibration samples versus first ones of the measurement points in the time interval;

determining a first lower confidence limit curve from the first curve;

fitting a second curve to a graph of the measured indicia of the quantity of a nucleic acid sequence being amplified in a second of the calibration samples versus second ones of the measurement points in the time interval;

determining a second lower confidence limit curve from the second curve;

determining first intersections between the first cutoff level and the first and second lower confidence limit curves; and determining the first points in the time interval from the first intersections.

40. The computer program product of claim 36, wherein said step of determining first points in the time interval comprises the steps of:

fitting a first curve to a graph of the measured indicia of the quantity of a nucleic acid sequence being amplified in a first of the calibration samples versus first ones of the measurement points in the time interval;

determining a first lower confidence limit curve from the first curve;

fitting a second curve to a graph of the measured indicia of the quantity of a nucleic acid sequence being amplified in a second of the calibration samples versus second ones of the measurement points in the time interval;

determining a second lower confidence limit curve from the second curve;

determining first intersections between the first cutoff level and the first and second lower confidence limit curves; and determining the first points in the time interval from the first intersections.

41. The computer program product of claim 40, wherein the calibration and test samples contain a fluorescent indicator therein; and wherein said step of measuring indicia of the quantities of a nucleic acid sequence being amplified comprises measuring fluorescence signals from the calibration and test samples at the measurement points in the time interval.

42. The computer program product of claim 41, wherein said amplifying step comprises amplifying a plurality of known quantities of a nucleic acid sequence in respective calibration samples and an unknown quantity of a nucleic acid sequence in a test sample, in parallel.

43. The computer program product of claim 42, wherein said step of determining which of the first or second points in the time interval better satisfies the statistical criterion comprises the step of determining which of the first or second points in the time interval provides a better linear fit against logarithms of the known quantities of a nucleic acid sequence in the calibration samples.

44. The computer program product of claim 43, wherein said step of determining which of the first or second points in the time interval provides a better linear fit comprises the steps of:

fitting a first regression line to a graph of the first points versus the logarithms of the known quantities of a nucleic acid sequence in the calibration samples;

fitting a second regression line to a graph of the second points versus the logarithms of the known quantities of a nucleic acid sequence in the calibration samples;

determining a standard deviation of the fit between the first points and the first regression line; and determining a standard deviation of the fit between the second points and the second regression line.

45. The computer program product of claim 44, wherein said step of determining first points in the time interval comprises the steps of:

fitting a first curve to a graph of the measured indicia of the quantity of a nucleic acid sequence being amplified in a first of the calibration samples versus first ones of the measurement points in the time interval;

fitting a second curve to a graph of the measured indicia of the quantity of a nucleic acid sequence being amplified in a second of the calibration samples versus second ones of the measurement points in the time interval;

determining first intersections between the first cutoff level and the first and second curves; and determining the first points in the time interval from the first intersections.

* * * * *